(12) United States Patent
Banning

(10) Patent No.: US 7,636,976 B2
(45) Date of Patent: Dec. 29, 2009

(54) POWER TOOTHBRUSH

(75) Inventor: Robert D. Banning, St. Louis, MO (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/489,906

(22) Filed: Jul. 20, 2006

(65) Prior Publication Data

US 2006/0254007 A1    Nov. 16, 2006

Related U.S. Application Data

(63) Continuation of application No. 10/331,799, filed on Dec. 30, 2002, now abandoned.

(51) Int. Cl.
*A61C 17/34* (2006.01)
(52) U.S. Cl. .............................. 15/22.1; 15/22.4; 15/28
(58) Field of Classification Search .................. 15/22.1, 15/22.2, 22.4, 167.1, 201, 28; 433/103, 118; 74/25, 48, 70
See application file for complete search history.

(56) References Cited

U.S. PATENT DOCUMENTS

| 793,587 | A | 6/1905 | Johnson |
| 1,212,001 | A | 1/1917 | Baxter |
| 1,255,028 | A | 1/1918 | Leonard et al. |
| 1,392,623 | A | 10/1921 | Cheatham |

(Continued)

FOREIGN PATENT DOCUMENTS

CN    2271352    7/1996

(Continued)

OTHER PUBLICATIONS

U.S. Appl. No. 10/237,902, filed Sep. 9, 2002, Robert D. Banning.

(Continued)

*Primary Examiner*—Shay L Karls
(74) *Attorney, Agent, or Firm*—Vladimir Vitenberg; George H. Leal; James C. Vago

(57) ABSTRACT

A power toothbrush with a drive train that is easy to manufacture, reliable in service and that enables multiple heads or other complex design or functional elements is provided. In an illustrative embodiment, the power toothbrush includes a sealed case that encloses a motor with a pinion gear joined to an eccentric link. This eccentric link can be a circular rack having an eccentric pin that rides in a slot on a drive plate. The drive plate is joined to a push rod, typically constructed of metal that passes up a hollow toothbrush shaft through an elastomeric seal to a head assembly. The head assembly includes one or more moving disks that are each connected to generally circular brush heads, which project outwardly from the head assembly. One disk receives a bent end of the drive shaft in a hole located eccentrically to the axis of rotation. When the circular rack rotates in a single direction, it drives the shaft in a reciprocating motion that, thereby, rotates the disk in a corresponding reciprocating circular motion about its axis. Additional disks can be linked by a short connecting shaft or link to the first disk via eccentric holes—other linkages, such as mating gears between disks can be used to simultaneously drive further disks, thereby providing a multiple moving-head power toothbrush.

10 Claims, 6 Drawing Sheets

U.S. PATENT DOCUMENTS

| | | | |
|---|---|---|---|
| 1,517,320 A | 12/1924 | Stoddart | |
| 1,553,456 A | 9/1925 | Metrakos | |
| 1,557,244 A | 10/1925 | Dominque | |
| 1,896,731 A | 2/1933 | Lippett | |
| 1,981,688 A | 11/1934 | Conti | |
| 1,997,352 A | 4/1935 | Fleet | |
| 2,044,863 A | 6/1936 | Sticht | |
| 2,140,307 A | 12/1938 | Belaschk et al. | |
| 2,172,624 A | 9/1939 | Robert | |
| 2,215,031 A | 9/1940 | Elmore | |
| 2,379,049 A | 6/1945 | Tompkins | |
| 2,435,421 A | 2/1948 | Blair | |
| 2,601,567 A | 6/1952 | Steinberg | |
| 3,115,652 A | 12/1963 | Zerbee | |
| 3,129,449 A | 4/1964 | Cyzer | |
| 3,159,859 A | 12/1964 | Rasmussen | |
| 3,160,902 A | 12/1964 | Aymar | |
| 3,178,754 A | 4/1965 | Cleverdon | |
| 3,195,537 A | 7/1965 | Blasi | |
| 3,242,516 A | 3/1966 | Cantor | |
| 3,379,906 A | 4/1968 | Spohr | |
| 3,398,421 A | 8/1968 | Rashbaum | |
| 3,509,874 A | 5/1970 | Stillman | |
| 3,524,088 A | 8/1970 | Ryckman | |
| 3,538,530 A | 11/1970 | Stemme | |
| 3,588,936 A | 6/1971 | Duve | |
| 3,592,188 A | 7/1971 | Barnett | |
| 3,935,869 A | 2/1976 | Reinsch | |
| 3,945,076 A | 3/1976 | Sung | |
| 3,978,852 A | 9/1976 | Annoni | |
| 4,027,348 A | 6/1977 | Flowers et al. | |
| 4,156,620 A | 5/1979 | Clemens | |
| 4,175,299 A | 11/1979 | Teague, Jr. et al. | |
| 4,274,173 A | 6/1981 | Cohen | |
| 4,281,987 A | 8/1981 | Kleesattel | |
| 4,326,314 A | 4/1982 | Moret et al. | |
| 4,346,492 A | 8/1982 | Solow | |
| 4,397,055 A | 8/1983 | Cuchiara | |
| 4,545,087 A | 10/1985 | Nahum | |
| 4,603,448 A | 8/1986 | Middleton et al. | |
| 4,791,945 A | 12/1988 | Moriyama | |
| 4,795,347 A | 1/1989 | Maurer | |
| 4,827,550 A | 5/1989 | Graham et al. | |
| 4,845,795 A | 7/1989 | Crawford | |
| 4,974,278 A | 12/1990 | Hommann | |
| 4,989,287 A | 2/1991 | Scherer | |
| 4,995,131 A | 2/1991 | Takeda | |
| 5,033,150 A | 7/1991 | Gross et al. | |
| 5,054,149 A | 10/1991 | Si-Hoe et al. | |
| 5,068,939 A * | 12/1991 | Holland | 15/22.1 |
| 5,070,567 A | 12/1991 | Holland | |
| 5,077,855 A | 1/1992 | Ambasz | |
| 5,088,145 A | 2/1992 | Whitefield | |
| 5,120,225 A | 6/1992 | Amit | |
| 5,138,734 A | 8/1992 | Chung | |
| 5,148,567 A | 9/1992 | Daub | |
| 5,170,525 A | 12/1992 | Cataro | |
| 5,186,627 A | 2/1993 | Amit et al. | |
| 5,226,206 A | 7/1993 | Davidovitz et al. | |
| 5,253,382 A | 10/1993 | Beny | |
| 5,259,083 A | 11/1993 | Stansbury, Jr. | |
| 5,276,932 A | 1/1994 | Byrd | |
| 5,301,381 A | 4/1994 | Klupt | |
| 5,311,633 A | 5/1994 | Herzog et al. | |
| 5,321,866 A | 6/1994 | Klupt | |
| 5,353,460 A | 10/1994 | Bauman | |
| 5,359,747 A | 11/1994 | Amakasu | |
| 5,383,242 A | 1/1995 | Bigler et al. | |
| 5,398,366 A | 3/1995 | Bradley | |
| 5,404,608 A | 4/1995 | Hommann | |
| 5,416,942 A | 5/1995 | Baldacci et al. | |
| 5,448,792 A | 9/1995 | Wiedemann et al. | |
| 5,465,444 A | 11/1995 | Bigler et al. | |
| 5,493,747 A | 2/1996 | Inakagata et al. | |
| 5,504,958 A | 4/1996 | Herzog | |
| 5,504,959 A * | 4/1996 | Yukawa et al. | 15/22.1 |
| 5,524,312 A * | 6/1996 | Tan et al. | 15/22.1 |
| 5,528,786 A | 6/1996 | Porat et al. | |
| 5,577,285 A | 11/1996 | Drossler | |
| 5,617,601 A | 4/1997 | McDougall | |
| 5,617,603 A * | 4/1997 | Mei | 15/22.1 |
| 5,625,916 A | 5/1997 | McDougall | |
| 5,679,991 A | 10/1997 | Wolf | |
| 5,687,442 A | 11/1997 | McLain | |
| 5,727,273 A | 3/1998 | Pai | |
| 5,732,432 A | 3/1998 | Hui | |
| 5,732,433 A | 3/1998 | Droessler et al. | |
| 5,738,575 A | 4/1998 | Bock | |
| 5,778,474 A | 7/1998 | Shek | |
| 5,784,743 A | 7/1998 | Shak | |
| RE35,941 E | 11/1998 | Stansbury, Jr. | |
| 5,836,030 A | 11/1998 | Hazeu et al. | |
| 5,842,244 A | 12/1998 | Hilfinger | |
| 5,842,245 A | 12/1998 | Pai | |
| 5,850,655 A | 12/1998 | Göcking et al. | |
| 5,862,558 A | 1/1999 | Hilfinger et al. | |
| 5,867,856 A | 2/1999 | Herzog | |
| 5,956,797 A | 9/1999 | Wilson | |
| 5,974,613 A | 11/1999 | Herog | |
| 5,974,615 A | 11/1999 | Schwarz-Hartmann et al. | |
| 6,000,083 A | 12/1999 | Blaustein et al. | |
| 6,049,936 A * | 4/2000 | Holley | 15/167.1 |
| 6,106,290 A | 8/2000 | Weissman | |
| 6,138,310 A | 10/2000 | Porper et al. | |
| 6,178,579 B1 | 1/2001 | Blaustein et al. | |
| 6,189,693 B1 | 2/2001 | Blaustein et al. | |
| 6,195,828 B1 | 3/2001 | Fritsch | |
| 6,237,178 B1 | 5/2001 | Krammer et al. | |
| 6,308,359 B2 | 10/2001 | Fritsch et al. | |
| 6,311,837 B1 | 11/2001 | Blaustein et al. | |
| 6,347,425 B1 | 2/2002 | Fattori et al. | |
| 6,360,395 B2 | 3/2002 | Blaustein et al. | |
| 6,371,294 B1 | 4/2002 | Blaustein et al. | |
| 6,421,865 B1 | 7/2002 | McDougall | |
| 6,421,866 B1 | 7/2002 | McDougall | |
| 6,434,773 B1 | 8/2002 | Kuo | |
| 6,446,294 B1 | 9/2002 | Specht | |
| 6,453,498 B1 | 9/2002 | Wu | |
| 6,463,615 B1 | 10/2002 | Gruber et al. | |
| 6,510,575 B2 | 1/2003 | Calabrese | |
| 6,536,066 B2 * | 3/2003 | Dickie | 15/22.1 |
| 6,546,585 B1 | 4/2003 | Blaustein et al. | |
| 6,564,940 B2 | 5/2003 | Blaustein et al. | |
| 6,574,820 B1 | 6/2003 | DePuydt et al. | |
| 6,623,698 B2 | 9/2003 | Kuo | |
| 6,725,490 B2 | 4/2004 | Blaustein et al. | |
| 6,751,823 B2 | 6/2004 | Biro et al. | |
| 6,760,945 B2 * | 7/2004 | Ferber et al. | 15/22.2 |
| 6,760,946 B2 | 7/2004 | DePuydt | |
| 6,836,917 B2 | 1/2005 | Blaustein et al. | |
| 6,889,401 B2 | 5/2005 | Fattori et al. | |
| 6,892,412 B2 | 5/2005 | Gatzemeyer et al. | |
| 6,892,413 B2 | 5/2005 | Blaustein et al. | |
| 6,928,685 B1 | 8/2005 | Blaustein et al. | |
| 6,944,901 B2 | 9/2005 | Gatzemeyer et al. | |
| 6,952,854 B2 | 10/2005 | Blaustein et al. | |
| 6,966,093 B2 | 11/2005 | Eliav et al. | |
| 6,983,507 B2 | 1/2006 | McDougall | |
| 7,124,461 B2 | 10/2006 | Blaustein et al. | |
| 7,137,163 B2 | 11/2006 | Gatzemeyer et al. | |
| 7,140,058 B2 | 11/2006 | Gatzemeyer et al. | |
| 7,140,059 B2 | 11/2006 | Scherl | |
| 7,150,061 B2 | 12/2006 | Kwong | |
| 7,162,764 B2 | 1/2007 | Drossler et al. | |

| Patent No. | Date | Inventor |
|---|---|---|
| 7,225,494 B2 | 6/2007 | Chan et al. |
| 7,258,747 B2 | 8/2007 | Vago et al. |
| 7,302,726 B2 | 12/2007 | Braun |
| 7,356,866 B2 | 4/2008 | Chan |
| 7,386,904 B2 | 6/2008 | Fattori |
| 7,392,562 B2 | 7/2008 | Boland et al. |
| 7,421,753 B2 | 9/2008 | Chan et al. |
| 7,430,777 B2 | 10/2008 | Scherl |
| 7,430,778 B2 | 10/2008 | Gatzemeyer et al. |
| 7,451,514 B2 | 11/2008 | Blaustein et al. |
| 7,520,016 B2 | 4/2009 | Kressner |
| 7,552,497 B2 | 6/2009 | Gatzemeyer et al. |
| 2001/0022277 A1 | 9/2001 | Blaustein et al. |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1* | 3/2002 | Blaustein et al. ............. 15/22.1 |
| 2002/0038772 A1 | 4/2002 | Blaustein et al. |
| 2002/0059685 A1 | 5/2002 | Paffrath |
| 2002/0078514 A1 | 6/2002 | Blaustein et al. |
| 2002/0138926 A1 | 10/2002 | Brown, Jr. |
| 2002/0152564 A1 | 10/2002 | Blaustein et al. |
| 2003/0000033 A1* | 1/2003 | Lev et al. ....................... 15/28 |
| 2003/0066145 A1 | 4/2003 | Prineppi |
| 2003/0074751 A1 | 4/2003 | Wu |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0140435 A1 | 7/2003 | Eliav et al. |
| 2003/0140437 A1 | 7/2003 | Eliav et al. |
| 2003/0154567 A1 | 8/2003 | Drossler et al. |
| 2003/0163881 A1 | 9/2003 | Driesen et al. |
| 2003/0163882 A1 | 9/2003 | Blaustein et al. |
| 2003/0182746 A1 | 10/2003 | Fattori et al. |
| 2003/0196283 A1 | 10/2003 | Eliav et al. |
| 2003/0213075 A1 | 11/2003 | Hui et al. |
| 2003/0226223 A1 | 12/2003 | Chan et al. |
| 2004/0045105 A1 | 3/2004 | Eliav et al. |
| 2004/0060137 A1 | 4/2004 | Eliav et al. |
| 2004/0074026 A1 | 4/2004 | Blaustein et al. |
| 2004/0083566 A1 | 5/2004 | Blaustein |
| 2004/0088807 A1 | 5/2004 | Blaustein et al. |
| 2004/0143917 A1* | 7/2004 | Ek ............................. 15/22.1 |
| 2004/0168272 A1 | 9/2004 | Prineppi |
| 2004/0177458 A1 | 9/2004 | Chan et al. |
| 2004/0177462 A1 | 9/2004 | Brown, Jr. |
| 2005/0000043 A1 | 1/2005 | Chan et al. |
| 2005/0000045 A1 | 1/2005 | Blaustein |
| 2005/0091771 A1 | 5/2005 | Blaustein et al. |
| 2005/0102776 A1 | 5/2005 | Mathur |
| 2005/0155167 A1 | 7/2005 | Gall |
| 2005/0268409 A1 | 12/2005 | Blaustein et al. |
| 2005/0278874 A1 | 12/2005 | Blaustein et al. |
| 2006/0032006 A1 | 2/2006 | Gall |
| 2006/0048314 A1 | 3/2006 | Kressner |
| 2006/0048315 A1 | 3/2006 | Chan et al. |
| 2006/0137118 A1 | 6/2006 | Blaustein |
| 2006/0254006 A1 | 11/2006 | Blaustein et al. |
| 2006/0254007 A1 | 11/2006 | Banning |
| 2007/0251033 A1 | 11/2007 | Gall |
| 2008/0010761 A1 | 1/2008 | Blaustein et al. |
| 2008/0016633 A1 | 1/2008 | Blaustein et al. |
| 2008/0078040 A1 | 4/2008 | Braun |
| 2009/0106923 A1 | 4/2009 | Boland |

FOREIGN PATENT DOCUMENTS

| | | |
|---|---|---|
| CN | 2236827 Y | 10/1996 |
| CN | 2271353 | 10/1996 |
| CN | 2274947 Y | 2/1998 |
| CN | 1187341 A | 7/1998 |
| CN | 2324987 | 6/1999 |
| CN | 2324988 | 6/1999 |
| CN | 2681701 Y | 3/2005 |
| DE | 3406112 | 8/1985 |
| DE | 3544256 | 8/1987 |
| DE | 4003305 | 8/1991 |
| DE | 29600236 | 4/1996 |
| DE | 29613608 | 11/1996 |
| DE | 29618755 | 3/1997 |
| DE | 19701964 | 7/1998 |
| DE | 298 09 977 | 2/1999 |
| DE | 19802904 | 7/1999 |
| DE | 19803311 | 8/1999 |
| EP | 259648 | 3/1988 |
| EP | 1053721 | 11/2000 |
| EP | 1059049 | 12/2000 |
| GB | 2247297 | 2/1992 |
| GB | 2290224 | 12/1995 |
| GB | 2319170 | 5/1998 |
| JP | 40-8743 | 8/1965 |
| JP | 57-89810 | 6/1982 |
| JP | 2-19241 | 2/1990 |
| JP | 02-218309 | 8/1990 |
| JP | 05-146313 | 6/1993 |
| JP | 05-146314 | 6/1993 |
| JP | 7-116020 | 5/1995 |
| JP | 7-116021 | 5/1995 |
| JP | 7-116023 | 5/1995 |
| JP | 07-116024 | 5/1995 |
| JP | 7-93892 | 10/1995 |
| JP | 8-322641 | 10/1996 |
| JP | 10-066704 | 3/1998 |
| JP | 2804940 | 7/1998 |
| KR | 1984-0004668 | 9/1984 |
| KR | 1986-0001137 | 6/1986 |
| KR | 1994-0013418 | 7/1994 |
| KR | 1995-0002814 | 2/1995 |
| KR | 1995-0010820 | 5/1995 |
| KR | 1997-0000408 | 1/1997 |
| KR | 1997-0000409 | 1/1997 |
| KR | 1995-0024551 | 4/1998 |
| KR | 143460 | 4/1998 |
| TW | 248031 | 12/1982 |
| TW | 233472 | 5/1983 |
| TW | 274724 | 4/1984 |
| TW | 256049 | 1/1993 |
| TW | 238504 | 6/1993 |
| TW | 253174 | 7/1994 |
| TW | 294031 | 11/1994 |
| TW | 239964 | 2/1995 |
| TW | 309753 | 7/1997 |
| TW | 330411 | 4/1998 |
| TW | 406557 | 9/2000 |
| TW | 257968 | 7/2006 |
| WO | WO 99/12492 | 3/1999 |
| WO | WO 01/06946 | 2/2001 |
| WO | WO 01/06947 | 2/2001 |
| WO | WO 01/21094 | 3/2001 |
| WO | WO 01/43586 | 6/2001 |
| WO | WO 02/102187 A1 | 12/2002 |
| WO | WO 03/020159 | 3/2003 |
| WO | WO 2004/045448 A1 | 6/2004 |

OTHER PUBLICATIONS

Bader, "Review of Currently Available Battery-Operated Toothbrushes", *Compend. Contin. Educ. Dent.*, vol. 13, No. 12, p. 1162, 1164-1169.

Photographs of electric toothbrush of BioBrush Industries (22 photographs).

Photos of Electric Toothbrush Head Refill.

Office Action for U.S. Appl. No. 10/903,222; P&G Case 8777C; dated Apr. 11, 2005.

Office Action for U.S. Appl. No. 10/903,222; P&G Case 8777C; dated Oct. 19, 2004.

Office Action for U.S. Appl. No. 11/200,680; P&G Case 8777CC; dated Sep. 22, 2005.
Office Action for U.S. Appl. No. 11/358,582; P&G Case 8777CCC; dated Mar. 17, 2008.
Office Action for U.S. Appl. No. 11/358,582; P&G Case 8777CCC; dated Apr. 14, 2006.
Office Action for U.S. Appl. No. 11/358,582; P&G Case 8777CCC; dated Apr. 17, 2007.
Advisory Action for U.S. Appl. No. 11/358,582; P&G Case 8777CCC; dated Jun. 9, 2008.
Advisory Action for U.S. Appl. No. 11/358,582; P&G Case 8777CCC; dated Jul. 27, 2007.
Office Action for U.S. Appl. No. 11/358,582; P&G Case 8777CCC; dated Sep. 5, 2008.
Office Action for U.S. Appl. No. 11/358,582; P&G Case 8777CCC; dated Sep. 6, 2007.
Office Action for U.S. Appl. No. 11/358,582; P&G Case 8777CCC; dated Sep. 29, 2006.
Office Action for U.S. Appl. No. 10/676,955; P&G Case 8778CC; dated Jan. 24, 2005.
Office Action for U.S. Appl. No. 10/676,955; P&G Case 8778CC; dated Jan. 24, 2005.
Office Action for U.S. Appl. No. 10/676,955; P&G Case 8778CC; dated Jul. 12, 2005.
Office Action for U.S. Appl. No. 10/676,955; P&G Case 8778CC; dated Jul. 29, 2004.
Office Action for U.S. Appl. No. 10/927,845; P&G Case 8778CCC2; dated Dec. 28, 2004.
Office Action for U.S. Appl. No. 10/929,288; P&G Case 8778CCC3; dated Mar. 18, 2005.
Office Action for U.S. Appl. No. 10/929,288; P&G Case 8778CCC3; dated Aug. 24, 2005.
Office Action for U.S. Appl. No. 11/514,742; P&G Case 8778CCC3C; dated Mar. 17, 2008.
Office Action for U.S. Appl. No. 11/514,742; P&G Case 8778CCC3C; dated Aug. 17, 2007.
Office Action for U.S. Appl. No. 11/514,742; P&G Case 8778CCC3C; dated Apr. 10, 2008.
Office Action for U.S. Appl. No. 11/006,972; P&G Case 8778CCC4; dated Mar. 24, 2005.
Office Action for U.S. Appl. No. 10/896,540; P&G Case 8778CCC; dated Oct. 4, 2004.
Office Action for U.S. Appl. No. 11/414,908; P&G Case 8829RRCC; dated May 23, 2007.
Office Action for U.S. Appl. No. 11/801,000; P&G Case 8829RRCCC; dated Jun. 20, 2008.
Office Action for U.S. Appl. No. 11/801,000; P&G Case 8829RRCCC; dated Sep. 26, 2008.
Office Action for U.S. Appl. No. 11/801,000; P&G Case 8829RRCCC; dated Oct. 26, 2007.
Office Action for U.S. Appl. No. 11/801,000; P&G Case 8829RRCCC; dated Dec. 5, 2008.
Office Action for U.S. Appl. No. 10/308,959; P&G Case 8880R; dated Feb. 16, 2006.
Advisory Action for U.S. Appl. No. 11/486,725; P&G Case 8880RC; dated Jan. 28, 2008.
Office Action for U.S. Appl. No. 11/486,725; P&G Case 8880RC; dated Jan. 28, 2009.
Office Action for U.S. Appl. No. 11/486,725; P&G Case 8880RC; dated Jan. 29, 2007.
Office Action for U.S. Appl. No. 11/486,725; P&G Case 8880RC; dated Apr. 10, 2008.
Office Action for U.S. Appl. No. 11/486,725; P&G Case 8880RC; dated Aug. 13, 2007.
Office Action for U.S. Appl. No. 11/893,469; P&G Case 8880RCC; dated Oct. 14, 2008.
Office Action for U.S. Appl. No. 11/893,469; P&G Case 8880RCC; dated Dec. 18, 2008.
Office Action for U.S. Appl. No. 11/410,808; P&G Case 9186C; dated Feb. 15, 2007.
Office Action for U.S. Appl. No. 11/410,808; P&G Case 9186C; dated Jul. 17, 2007.
Office Action for U.S. Appl. No. 11/015,111; P&G Case 9487; dated Nov. 24, 2008.
Office Action for U.S. Appl. No. 11/220,219; P&G Case 9770; dated Oct. 20, 2008.
Office Action for U.S. Appl. No. 10/367,373; dated Mar. 9, 2004.
Office Action for U.S. Appl. No. 09/425,423; P&G Case Z-3735; dated Jan. 31, 2002.
Office Action for U.S. Appl. No. 09/425,423; P&G Case Z-3735; dated Aug. 14, 2002.
Office Action for U.S. Appl. No. 10/331,799; P&G Case Z-3557; dated Apr. 19, 2005.
Office Action for U.S. Appl. No. 10/331,799; P&G Case Z-3557; dated Oct. 14, 2005.
Office Action for U.S. Appl. No. 10/331,799; P&G Case Z-3557; dated Feb. 23, 2006.
Office Action for U.S. Appl. No. 11/295,907; P&G Case 9853; dated Jun. 5, 2009.
Office Action for U.S. Appl. No. 09/993,167; P&G Case 8778; dated Dec. 18, 2002.
Office Action for U.S. Appl. No. 09/993,167; P&G Case 8778; dated Apr. 16, 2003.

* cited by examiner

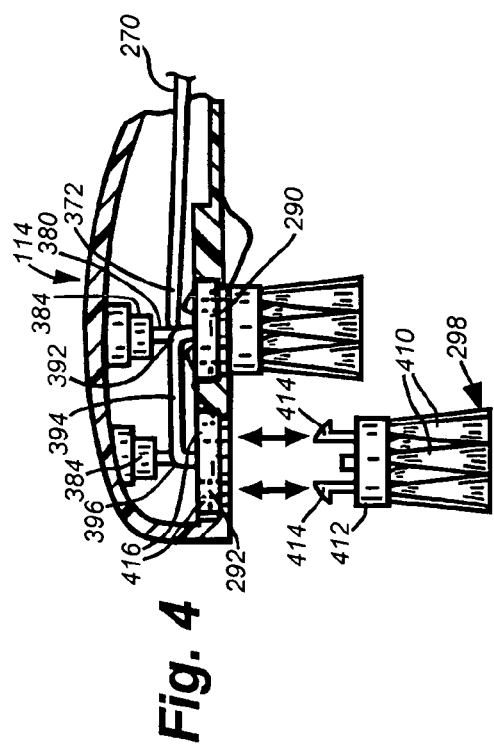
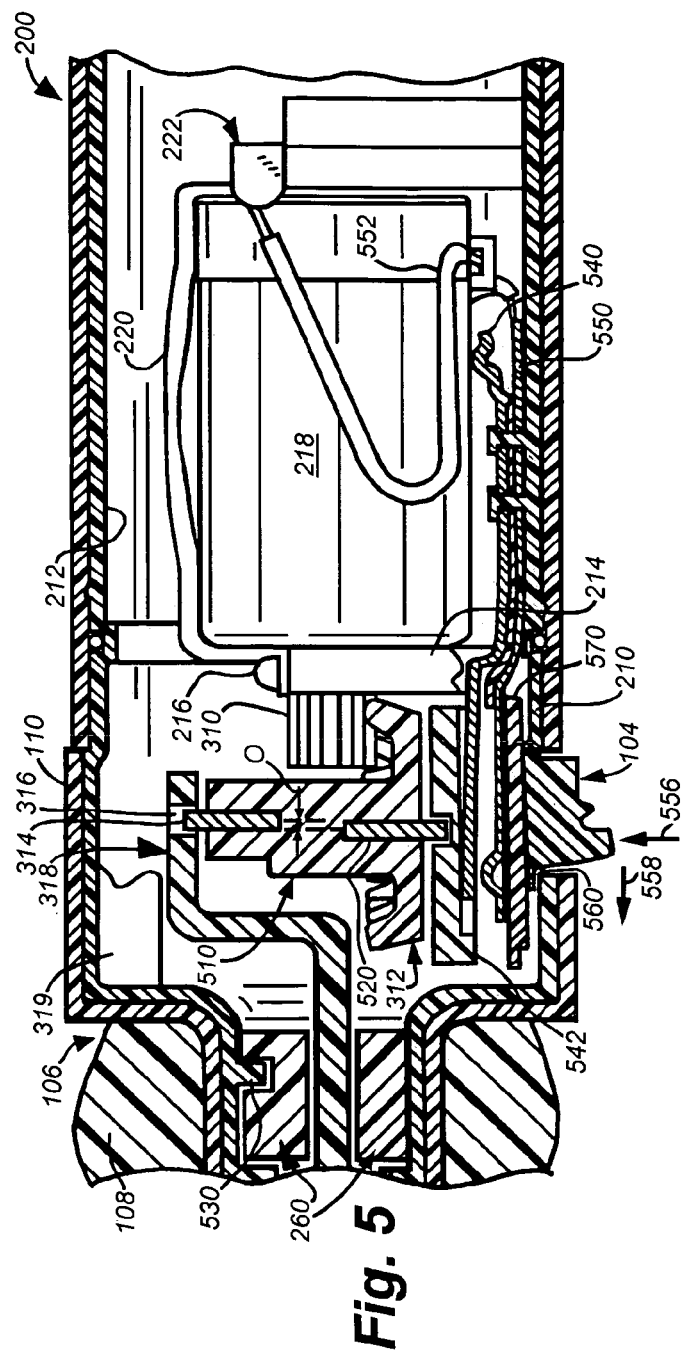

POWER TOOTHBRUSH

This application is a continuation of U.S. application Ser. No. 10/331,799, filed Dec. 30, 2002, now abandoned which is incorporated herein by reference.

FIELD OF THE INVENTION

This invention relates to toothbrushes and more particularly to inexpensive battery-powered power toothbrushes.

BACKGROUND OF THE INVENTION

Powered toothbrushes are becoming an increasingly desirable item for both adults and children. A variety of inexpensive semi-disposable and fully disposable powered toothbrushes are now available on the market. In order to interest children in developing good oral hygiene habits, many toothbrushes, including powered toothbrushes, are provided with decoration relevant to childrens' tastes. One of the more elaborate and desired forms of decoration is a sculpted feature applied to a portion of the brush handle. Such sculpted features can represent well-known cartoon characters or any other relevant three-dimensional subject matter including desirable toys.

Some important considerations in any disposable or semi-disposable power toothbrush design include appearance, reliability, and ease of manufacture. Thus, some designs may be easy to manufacture, but unreliable, and vice versa. The possibility of adding more-complex features, such as multiple moving brush heads is desirable, but may reduce cost ore reliability. A cost-effective design, with complex function (e.g. reciprocating motion, multiple heads, etc.), aesthetic appeal, reliability and ease of manufacture is an object of this invention.

SUMMARY OF THE INVENTION

This invention overcomes the disadvantages of the prior art by providing a power toothbrush with a drive train that is easy to manufacture, reliable in service and that enables multiple heads or other complex design or functional elements. In an illustrative embodiment, the power toothbrush includes a sealed case that encloses a motor with a pinion gear joined to a circular rack that drives an eccentric link that converts unidirectional rack rotation into bi-directional reciprocating linear motion. In one embodiment, the eccentric link is an eccentric pin mounted on the rack that rides in a slot on a drive plate. The plate is joined to a push rod, typically constructed of metal that passes up a hollow toothbrush shaft through an elastomeric seal to a head assembly. The head assembly includes one or more moving disks that are each connected to generally circular brush heads, which project outwardly from the head assembly. One disk receives a bent end of the drive shaft in a hole located eccentrically to the axis of rotation. When the circular rack rotates in a single direction, it drives the shaft in a reciprocating motion that, thereby, rotates the disk in a corresponding reciprocating circular motion about its axis. Additional disks can be linked by a short connecting link (a rod, gear train, etc.) to the first disk via eccentric holes—other linkages, such as mating gears between disks can be used to simultaneously drive further disks, thereby providing a multiple moving-head power toothbrush.

In an illustrative embodiment, the case comprises a pair of halves that hold the drive train motor and associated components in position and are sealed by welding or other adhesion techniques. The bottom of the case may be open to receive batteries. An outer cover sleeve is fitted over the lower portion of the case to seal the bottom and provide a decorative outer shell that also provides the handle. A sealing ring may be provided between the case and outer sleeve to prevent infiltration of moisture. Likewise, the toothbrush shaft and head assembly can include a plurality of slots or holes for draining moisture away from the regions outside the elastomeric shaft seal. A decorative, sculpted topper can be provided above the outer sleeve mounted along the toothbrush shaft with an apron that extends along the case toward the upper edge of the outer sleeve.

BRIEF DESCRIPTION OF THE DRAWINGS

The invention description below refers to the accompanying drawings, of which:

FIG. 4 is a more detailed cross section of the head assembly of the power toothbrush of FIG. 1;

FIG. 5 is a more detailed cross section of the motor and drive gear assembly of the power toothbrush of FIG. 1;

DETAILED DESCRIPTION OF AN ILLUSTRATIVE EMBODIMENT

The present application is related to commonly assigned U.S. patent application Ser. No. 10/237,902, filed Sep. 9, 2002, by Robert D. Banning entitled TOPPER FOR A POWER TOOTHBRUSH, the teachings of which are expressly incorporated by reference.

Figure 1:
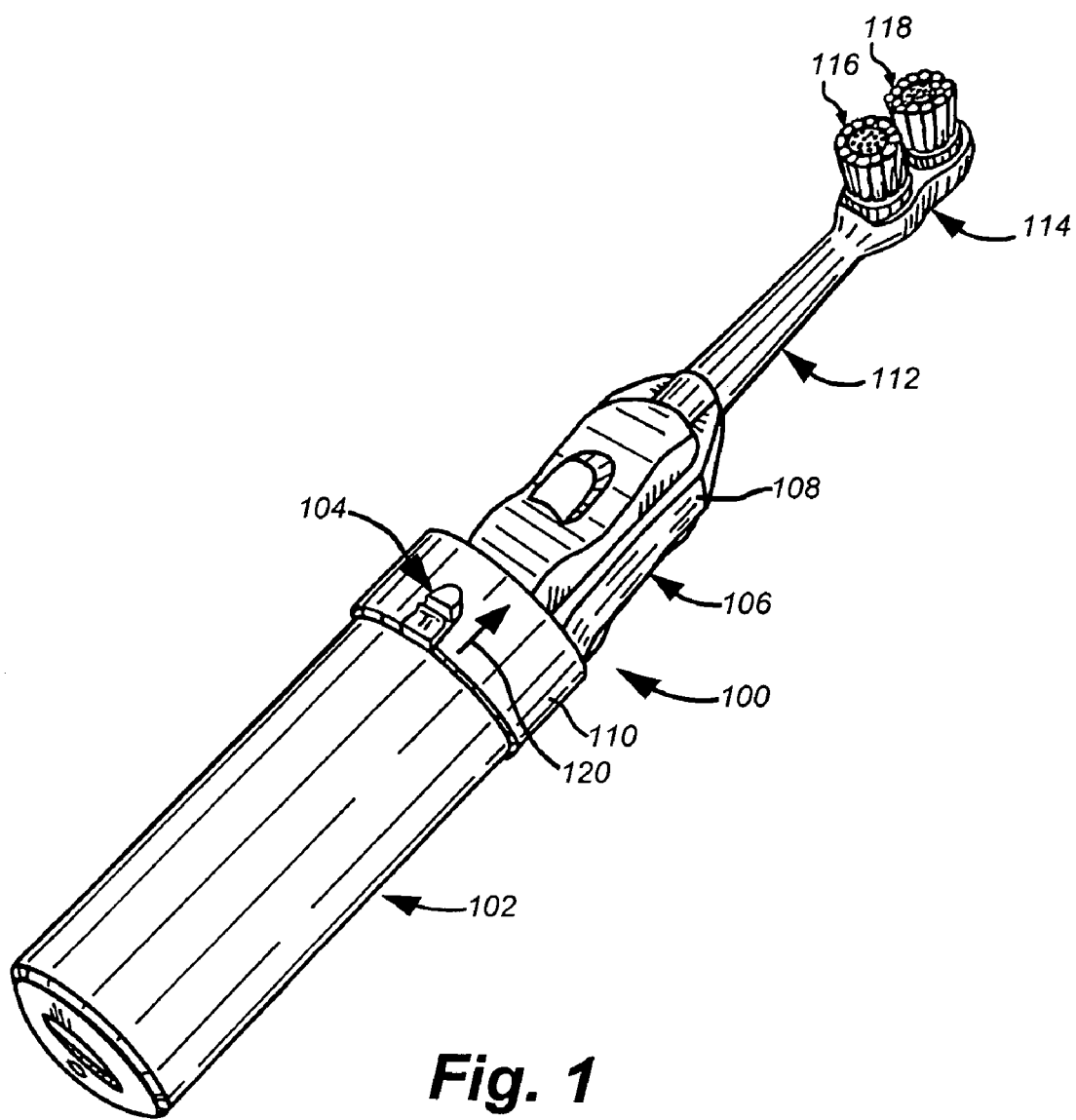
FIG. 1 is a perspective view of a power toothbrush according to an embodiment of this invention.
Figure 2:
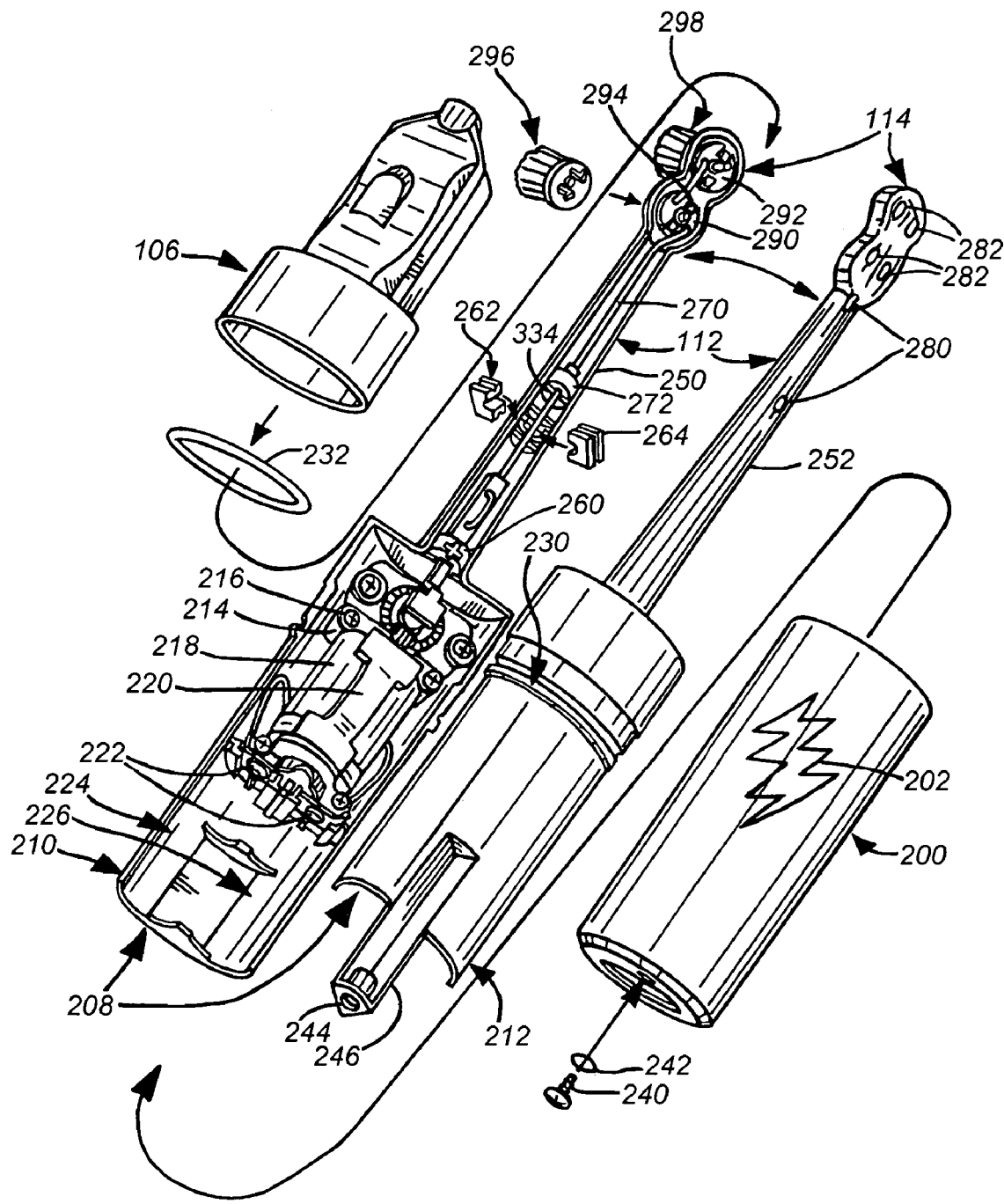
FIG. 2 is an exploded perspective view of the power toothbrush of FIG. 1.

FIG. 1 shows a power toothbrush 100 according to an illustrative embodiment of this invention. The toothbrush includes a handle region 102, an on/off switch 104, a decorative topper 106 that includes a sculpted feature 108 (in this case a race car) and an apron that is attached to the sculpted feature 110. The topper, and its assembly, is described further with reference to the above-incorporated U.S. patent application Ser. No. 10/237,902. The topper 106 is placed over a hollow toothbrush shaft 112 ending in a head assembly 114. The head assembly, in this embodiment, includes two rotationally moving brush heads 116 and 118. The switch 104, when depressed causes the heads to rotate under power of an internal motor to be described below. The switch 104 has a momentary contact position when it is depressed directly downwardly toward the case, and a constant-on position when it is depressed and slid toward the topper (arrow 120) so that a forward lip catches the shoulder on the case. With further reference to FIG. 2, the drive train and other internal components of the brush 100 are shown in further detail. Note that the handle region is defined by an outer sleeve 200. The outer sleeve can include a graphic 202 or a three-dimensional sculpted design (described further below with reference to, for example, FIG. 7). Such a sculpted design can extend outwardly from the ellipse defined generally by the sleeve 200. In certain embodiments, the sculpted design can also extend inwardly. The sleeve 200 encloses the lower or bottom portion of the case (collectively 208). The case includes a pair of case halves 210 and 212 that are typically formed from molded plastic or another like material. In this embodiment, one half of the case 210 includes a series of raised lugs (such as lug 214) for receiving screws (such as screw 216). The screws retain a DC motor 218. The DC motor is retained by a metal retaining plate 220 and is interconnected to a battery contact assembly 222. Semi-circular wells, 224 and 226, are provided for receiving a pair of batteries. In this case, the batteries are AA-size, but the actual size of the batteries are highly variable. In addition, rechargeable batteries can be provided in an alternate embodiment or batteries can be omitted in favor of a connecting cord to line-voltage or, preferably, a low-voltage transformer. The case halves 210 and 212 include a circumferential recess 230 for receiving a sealing ring 232. In this embodiment, the sealing ring can comprise a conventional O-ring formed from polyurethane or another suitable material. The sealing ring seals the case halves 210 and 212 with respect to the inner wall of the outer sleeve 200 so that water can not infiltrate the interior of the case. A screw 240 is provided at the bottom of the sleeve 200. A small sealing ring 242, prevents water from passing through the screw hole when the screw is firmly secured to a receiving hole 244 on an extension 246 of the case half 212.

The case narrows to a pair of hollow half sections 250 and 252 of the toothbrush shaft 112. Within the shaft half sections 250, 252 are a series of shaft guides 260, 262 and 264. These reside in slots that are provided within the hollow toothbrush shaft to retain the guides in place. A reciprocating drive shaft 270 (described further below) is guided in a linear reciprocating motion by the guides 260, 262 and 264. The drive shaft 270 is generally straight along the majority of its length, extending along a linear axis of movement. Approximately half way along the length of the shaft 270 is provided a surrounding seal 272 constructed from an elastomeric material such as silicone. The seal is shaped generally as a cup having a cup section 333 that includes a relatively thin circumferential wall and hollowed interior with a hole sized closely to or slightly smaller than the diameter of the drive shaft 270. Note that the hollowed cup end faces toward the motor in this embodiment and abuts the adjacent retaining wall or abutment 334. The seal allows the shaft 270 to slide in a reciprocating motion, but prevents moisture from penetrating into the lower portion of the hollow toothbrush shaft or case. It is retained by the walls or abutments 334 and 335 (FIG. 3), to restrict linear movement. The natural pliability of the cup allows it to flex freely within the limited range of linear reciprocating motion experienced by the drive shaft, thus maintaining a seal while allowing the linear motion to occur with minimal resistance. In addition, the seal 272 allows an acceptable range of side-to-side motion (transverse/orthogonal) to the extension axis of the drive shaft 270. The hole diameters for the walls 334 and 335 are also sized with this transverse motion in mind. This side-to-side motion is generated due to the pivotless link between the shaft 270 and brush head disk 290. Positioned distally from the seal 272 are provided various drain slots 280 and 282 along the toothbrush shaft 112 and head assembly 114. These slots prevent water or other moisture penetrating the distal end of the shaft from being retained.

Note that all walls or abutments along the toothbrush shaft 112 are sized to include appropriately sized cutouts (either circles or another appropriate shape). These cutouts are sized and arranged to enable the drive shaft and drive plate to move freely through the cutouts (in both axial and side-to-side motion as appropriate), but to adequately retain and/or seal the various guides and seals described herein.

Figure 3:
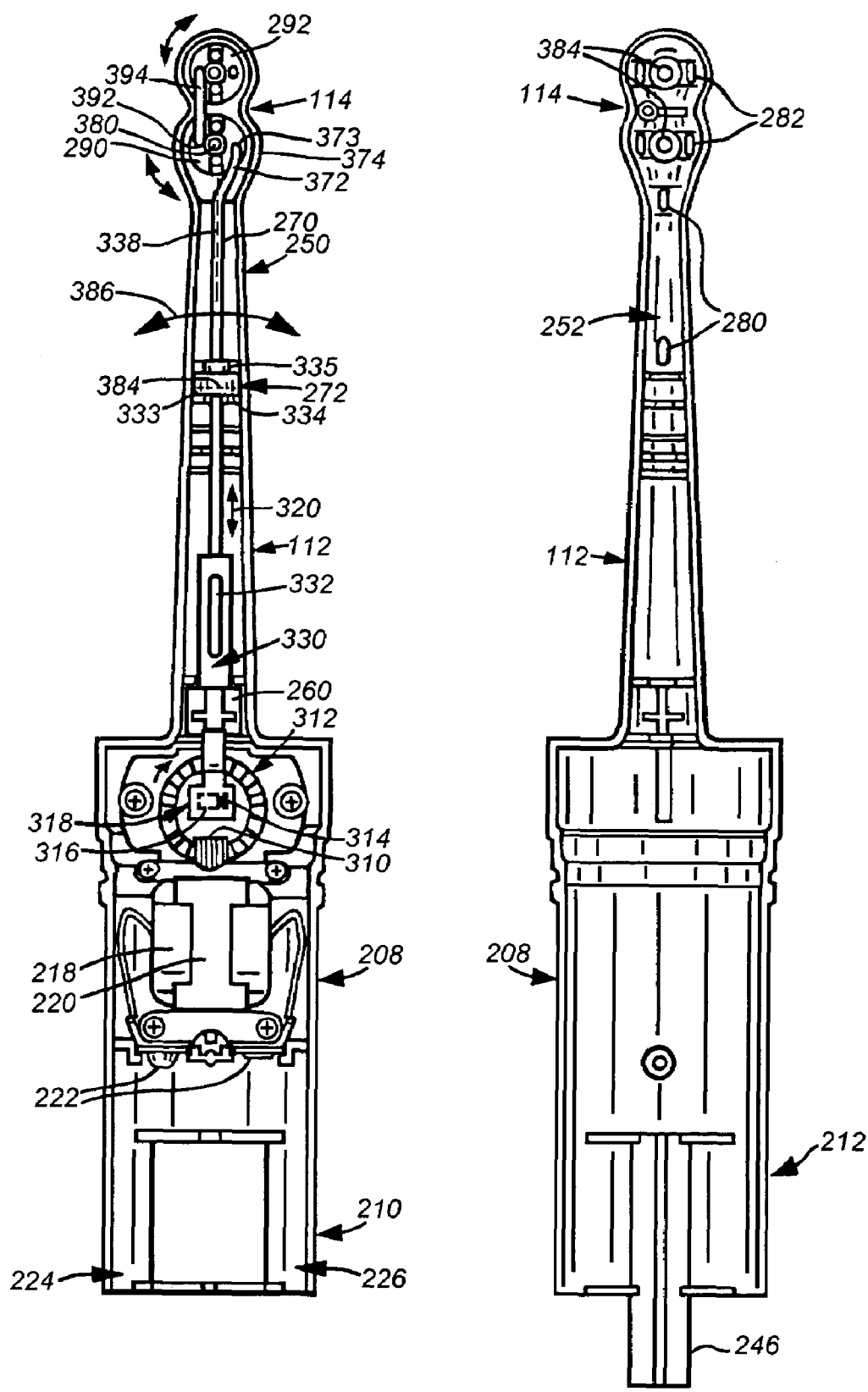
FIG. 3 is a breakaway plan view of the separate halves of the case of the power toothbrush of FIG. 1.

Within the head assembly 114 are a pair of rotating disks, 290 and 292 in communication with the drive shaft 270. The disks are joined by a short connecting link 294 so that motion applied to the disk 290 by the shaft 270 is transmitted to the more-distal disk 292. Each disk is in turn connected by a snap fitting to a brush head 296 and 298. With further reference to FIG. 3, the drive train will now be described in further detail.

The motor 218 is connected via a pinion gear 310 to a rotary rack 312. As shown also in FIG. 5, the rack includes a raised pedestal 510 with an eccentrically mounted pin 314. As used herein the term "eccentric" shall refer to a position on a rotating body that is offset with respect to the central axis of rotation of that body. The pin engages a cross-slot 316 in a drive plate 318. The drive plate 318 rises to the level of the pedestal top through a series of right-angled bends from a more distal portion that is even with the axis of the toothbrush shaft 112. As the pinion gear 310 causes the rack 312 to rotate in a constant direction, the pin 314 drives the drive plate 318 to generate an axial, reciprocating motion (double arrow 320). The drive plate 318, which can be constructed from a self-lubricating plastic such as Delrin™ or nylon steps down from the raised base 312 to move centrally through the toothbrush shaft past the guide 260.

Referring to FIG. 3, within the toothbrush shaft and beyond the guide 260, the distal portion 330 of the drive plate 318 is interconnected to a semi-flexible metal rod 332, which provides the main portion of the drive shaft 270. The distal portion of the drive shaft 270 includes a bend 372. The bend diverts the end 373 of the drive shaft away from the shaft's central axis of extension 338 and generally along the inner side of the widened, curving wall 374 of the head assembly. In this manner, the end of the drive shaft is eccentric to the central axis 380 of the first disk 290. Note that the opposing half 252 of the hollow toothbrush shaft 112 includes raised holes or dogs 384 for receiving an axle of each of the disks 290 and 292. Each axle is constructed from metal rod in an illustrative embodiment, but a molded axle (plastic, etc.) can be provided to each brush head disk in an alternate embodiment.

The end 373 of the drive shaft 270 is bent into a downward L-shape (see FIG. 4) so that it resides within an eccentric hole within the first disk 290. On an opposite side of the first disk 290, is a second eccentric hole for receiving the L-shaped, bent end 392 of a connecting link or shaft 394. The opposing end, 396, of the short connecting link 394 is received by a corresponding eccentric hole in the second, more-distal disk 292. In this manner, when a reciprocating motion is directed along the axis of the drive shaft 270, it causes the first disk to rotate and, hence, the first disk causes the second disk to rotate. The connecting shaft 394 can be broadly defined herein as a "connecting link" between brush heads. According to an alternate embodiment, this connecting link can comprise, for example, one or more gears in a gear train between disks. If two geared heads are connected together, they cause a counter-rotating effect that may be desirable in certain embodiments. Additional brush heads can be provided according to alternate embodiments arranged either linearly along the length of the head assembly or in another geometric shape such as a triangle.

As described generally above, the size and shape of the cup seal 272 and the relative diameters of the walls 334 and 335 accommodate the solid, unpivoted link between the disk 290 and end 373 of the drive shaft 270. The side-to-side motion (double arrow 386) generated as the disk 290 rotates and the shaft rides in its eccentric hole through a desired range of arcuate rotation. In other words, the hole will translate orthogonally to the axis of extension of the drive shaft 270 as the disk rotates about its axis.

Note that in one embodiment, the cup seal 272 can include, within it's cup a flush-fitting ring or washer 384 (shown in phantom), typically constructed of a lubricating plastic that prevents excessive side-to-side flexure that may otherwise undesirably kink or bend the seal and allow moisture to pass between the seal 272 and wall 334. Such undesirable bending tends to increase when the travel distance of the drive shaft 270 is increased to increase the rotational distance of the heads.

With further reference to the details of FIGS. 4 and 5, further details are shown. As described generally above, FIG. 4 shows a toothbrush head 298 having a set of bristles 410 in a generally circular pattern anchored in a base 412. The base includes a pair of prongs 414 that interlock with corresponding holes 416 in the disk 292. This enables easy assembly of completed heads two disks after the underlying brush drive train has been constructed. In certain embodiments, it is contemplated that the heads may be replaceable by providing an appropriate release mechanism for the base 412.

With particular reference to FIG. 5, the drive train motor and gear assembly are shown in greater detail. In particular, the motor 218 that drives a horizontal pinion gear 310, engages the rotary rack 312. The raised pedestal 510 supports a metal pin 314 that rides within the slot 316 on the drive plate 318. Note that the center axis of the pin 314 is offset (e.g. eccentric) with respect to the center axis of the rack's metal axle pin 520 (See offset O). In this manner, rotation of the rack 312 about the axle 520 causes the pin 314 to move in a circular path with respect to the center of the axle 520. Accordingly, the pin drives the drive plate 318 in a reciprocating linear motion as it rides along the slot 316. The degree of offset if variable. In general, the pin can be offset between $1/32$ and $1/16$ of an inch. However, variety of offset values can be chosen. The amount of offset varies the amount of linear reciprocating distance traveled by the drive shaft 270. Similarly, the spacing of the end 373 of the drive shaft, with respect to the center axis 380 (see FIG. 3) of the brush head disk 290, determines the amount of angular rotation of the disk and its brush head. In this embodiment, the hole for receiving the end 373 in the disk is offset approximately $1/8$ inch from the center of the axis of rotation of the disk. Typically, a reciprocating rotational distance of between 5 and 30 degrees is generated by the power toothbrush according to this embodiment. A variety of rotational and linear distances are, however, contemplated.

The drive plate 318 is retained against upward movement out of engagement with drive pin 314 by an opposing projection 319 (FIG. 3, also shown in fragmentary view in FIG. 5). The guide 260 also serves to hold the drive plate 318 in position. The guides 260, 262 and 264 are constructed from a low-friction material such as Delrin or nylon. However lubricating grease can also be provided to any of the bearing or intermeshing surfaces herein.

Note also that the guide 260 comprises two halves that enable the drive plate 318 to be mounted therebetween during assembly. A cruciform projection 530 in at least one wall of the toothbrush shaft maintains proper rotational alignment of the guide half. A similar projection can be provided to the bottom half (not shown).

The motor makes contact with a switch contact plate 540, that extends forwardly to the rack base 542. A well is provided in the rack base 542 for receiving the end of the contact plate. An opposing contact plate 550 extends from the battery contacts 222 via a wire 552 to the switch assembly 104. The end of the plate 550 is sprung so as to bias the switch outwardly away from the opposing contact plate 540. By applying a downward force (arrow 556) the plates are brought into contact. The switch button is slideable forwardly (arrow 558) when it is depressed so that a shoulder 560 becomes engaged to the underside of the case, thus holding the button in place with the contact plates 540 and 550 in engagement (thereby making electrical contact). In this manner, both a momentary contact position is enabled (by a simple downward push) and a full-time on position is enabled (by a downward push followed by a forward slide). An elastomeric seal 570 is provided between the button and the contact plate to both cushion the button and prevent moisture infiltration.

It is further contemplated, in an alternate embodiment (not shown), that the drive plate and pin (318 and 314) can be replaced with a connecting rod that is pivotally mounted between the drive shaft (270) and the rack 312 with the rack's pivot offset from the rack's axis of rotation. Like the above-described slot and eccentric pin arrangement, this type of linkage provides the desired conversion of a unidirectional rotation (by the rack) into a linear reciprocating motion (for the drive shaft). Accordingly, the term "eccentric link" when used herein shall define any acceptable arrangement that converts unidirectional rotation of a rack or other rotating, driven disk into a linear reciprocating (bi-directional) motion of an operatively connected drive shaft.

Figure 6:
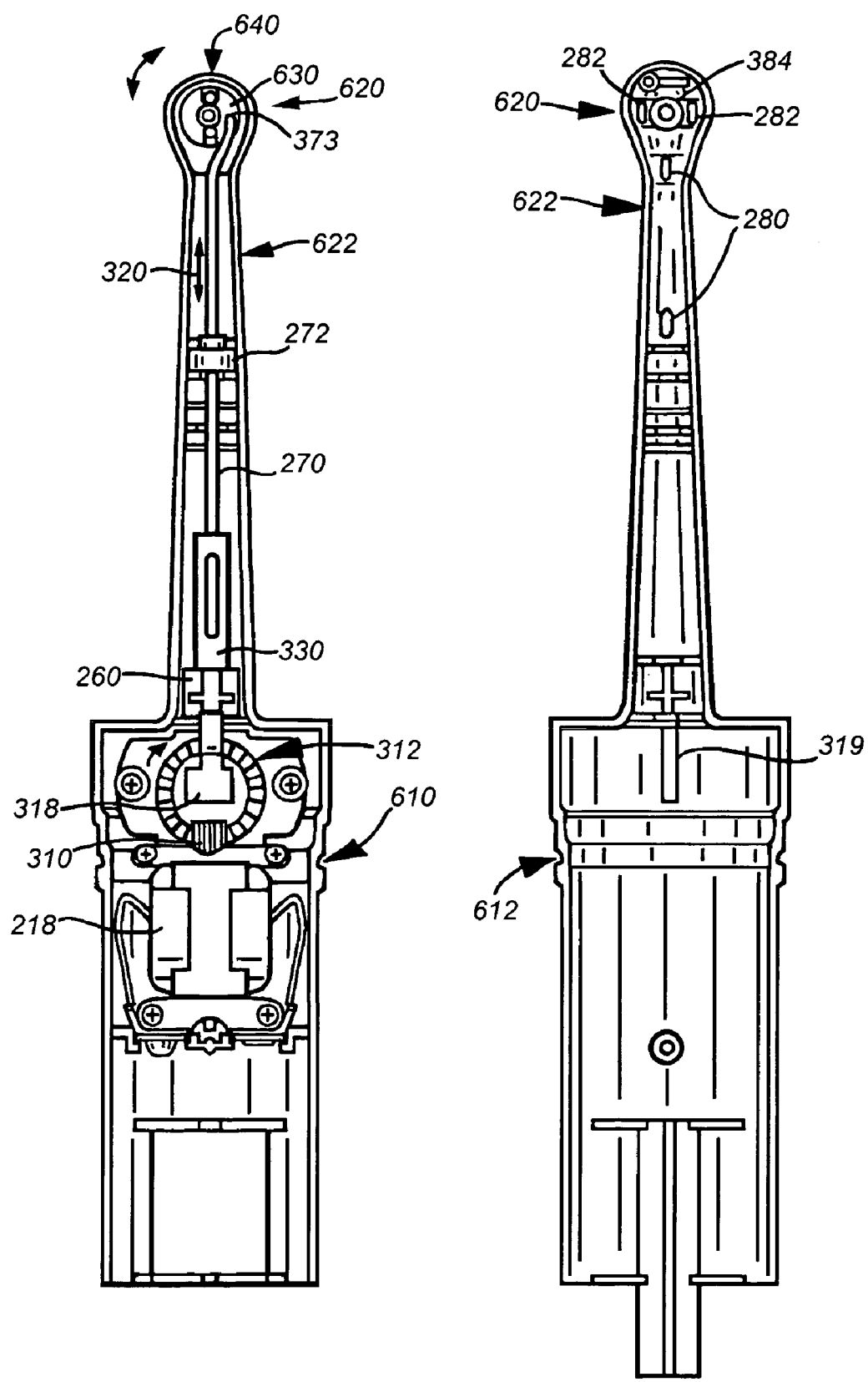
FIG. 6 is a plan view of the halves of a case for a power toothbrush having a single moving head according to an alternate embodiment.

FIG. 6 shows an alternate embodiment of the toothbrush according to this invention in which the case halves 610 and 612 include a similar drive train having, generally, a motor 218, a rack 312, pinion gear 310, drive plate 318 and drive shaft 270. However, a single brush head is provided in the head assembly 620 extending from the hollow toothbrush shaft 622. The shaft end 373 is mounted in a disk 630 that, in this embodiment, does not require an opposing hole for a connecting link. The case ends (end 640) such that it supports only a single head. The exact size and configuration of the end of the head assembly 620 is highly variable. All other elements of the toothbrush according to FIG. 6 are similar to those in the toothbrush of the embodiment of FIGS. 1-5. Accordingly, like references are used for such elements.

Figure 7:
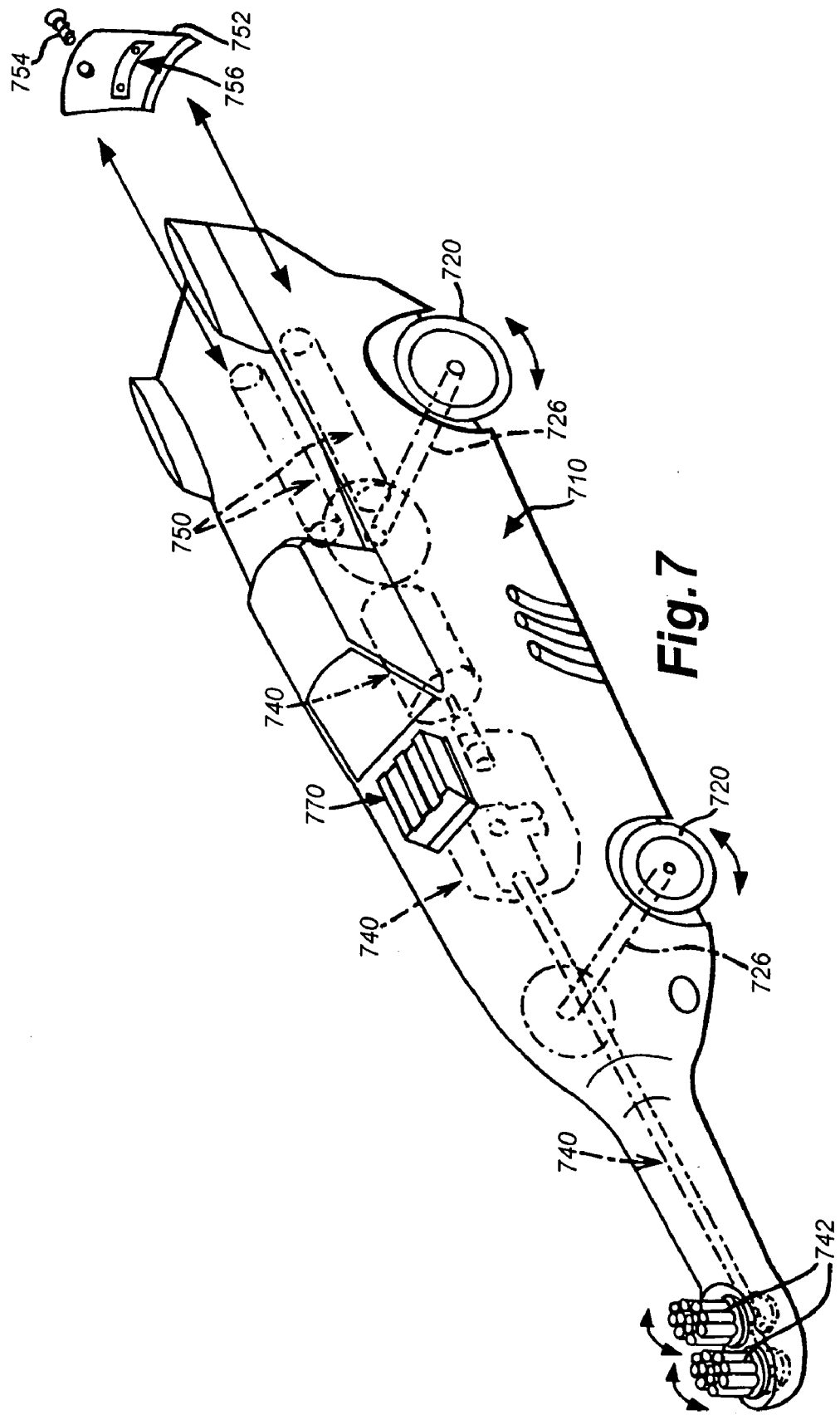
FIG. 7 is an exposed schematic perspective view of a power toothbrush having a sculpted handle in the shape of a race car and including a drive train in accordance with an embodiment of this invention.

FIG. 7 details a power toothbrush according to another embodiment of this invention. This toothbrush has a stylized handle 710 in the shape of a racing car or other desirable sculpted shape (such as a character). In this embodiment, the car includes wheels 720 that turn in contact with the ground. Through-axles 726 are shown in phantom, mounted to the case 710 via holes in the case side. The case can be constructed in a variety of ways. In one embodiment, it is constructed from two solid halves that extend along the entire length similar to the case 210 and 212. No outer sleeve is provided in such an embodiment, and instead, the two halves are joined together by welding, fasteners or another acceptable means once the drive train 740 (shown schematically in phantom) is assembled within the case.

In this embodiment, the drive train is structurally and/or functionally similar to that shown and described in the embodiments of FIGS. 1-6. That is, the drive train includes a motor, a rotating rack with an eccentric drive pin, a slotted drive plate, an interconnected drive shaft and one or more driven disks connected to toothbrush heads 742.

Where a solid case with no outer sleeve is provided, batteries 750 (shown in phantom) can be inserted and removed via a rear plate 752 having a screw 754 that engages the rear of the case 710 and that includes a battery contact plate 756. An O-ring or other seal can be provided around the plate to prevent water infiltration. In an alternate embodiment, the decorative handle (i.e., the car body) can be slid over a case such as the case 210 and 212 shown in FIG. 3. In such an embodiment, the topper can be sculpted as the front end of the car.

In the embodiment of FIG. 7, an on/off button 770 is provided on top of the car in the form of a stylistic air intake. The location of the button 770 on the case is highly variable. However, its function (momentary and full-time contact) is similar to that described with reference to the embodiments of FIGS. 1-6.

The foregoing has been a detailed description of various embodiments of the invention. A variety of modification and additions can be made without departing from the spirit and scope thereof. For example, it should be clear that a wide variety of shapes can be provided to both the topper and to the main handle of the toothbrush. The exact size and dimension of various drive train features is widely variable, as is the length of the toothbrush shaft. In general, the toothbrush shaft should be able to fit within the mouth of a small child or adult where applicable. Likewise, the handle and buttons should be sized so that they accommodate the chosen user. The size and shape of the on/off button are also widely variable, as is their method of operation. Accordingly, this description is meant only to be taken as way of example and not to otherwise limit the scope of the invention.

What is claimed is:

1. A power toothbrush comprising:
   a case defining two case halves with a hollow toothbrush shaft and head assembly at a distal end of the toothbrush shaft, and having mounted therein a motor with a pinion gear;
   a rack that is driven in a unidirectional rotation by the pinion gear and having an eccentric link that converts the unidirectional rotation of the rack into a bi-directional reciprocating linear motion;
   a drive shaft extending through the toothbrush shaft to the head assembly interconnected to the eccentric link that moves in the bi-directional reciprocating linear motion in response to the rotational movement of the rack;
   a first disk located at the head assembly, the first disk being interconnected to a distal end of the drive shaft at a point that is offset from an axis of extension of the drive shaft and remote from an axis of rotation of the first disk, the first disk being interconnected to a first brush head for rotation in a plane substantially parallel to the axis of extension of the drive shaft;
   a second disk located remote from the first disk and interconnected to a second brush head; and
   a connecting rod pivotally connected to the first disk and the second disk, the connecting rod being disposed, in its entirety, and in plan view, at a distance from the axis of extension of the drive shaft in a direction transverse thereto, so that the rotation of the first disk causes concurrent rotation of the second disk in the plane substantially parallel to the axis of extension of the drive shaft.

2. The power toothbrush of claim 1 wherein the connecting rod is configured such that the first disk and the second disk rotate in opposite directions.

3. The power toothbrush of claim 1 wherein the connecting rod is configured such that the first disk and the second disk rotate in the same direction.

4. The power toothbrush of claim 1 wherein the point of the first disk is offset from the axis of rotation of the first disk by approximately 3.175 mm.

5. The power toothbrush of claim 1 wherein the first disk and/or the second disk reciprocate through a rotational distance of between 5 and 30 degrees.

6. The power toothbrush as set forth in claim 1 wherein the drive shaft includes a cup-shaped seal that surrounds the drive shaft, the seal being retained by walls within the toothbrush shaft, the seal being constructed and arranged to flex between the walls in response to the reciprocating linear motion and to resist passage of moisture from the distal end of the toothbrush shaft toward a portion of the case containing the motor.

7. The power toothbrush as set forth in claim 1 further comprising an outer sleeve that is sized and arranged as a handle, the sleeve being adapted to slide over the case halves and seal an open bottom of the case, the case halves including a sealing ring adapted to seal between an outer surface of the case halves and an inner surface of the sleeve.

8. The power toothbrush as set forth in claim 1 further comprising an on/off button assembly extending through a hole in the case having a spring contact adapted to allow momentary contact with a motor contact when a button is depressed in a first direction and having a shoulder that engages an inner wall of the case when the button is slid in a second, orthogonal direction so as to retain the spring contact against the motor contact to produce a full-time contact.

9. The power brush as set forth in claim 1 wherein the drive shaft includes a bend portion extending distally to the hole of the disk from a portion of the shaft aligned with the axis of extension, the bend portion being free of a pivot or movable interconnection with respect to the aligned portion of the shaft.

10. The power toothbrush as set forth in claim 9 wherein the drive shaft includes a cup-shaped seal that surrounds the drive shaft, the seal being retained by walls within the toothbrush shaft, the seal being constructed and arranged to flex between the walls in response to the reciprocating linear motion and to resist passage of moisture from the distal end of the toothbrush shaft toward a portion of the case containing the motor and wherein the walls include cutouts that are sized and arranged, and the seal is constructed and arranged, so as to allow side-to-side movement of the shaft transverse to the axis of extension in response to rotation of the first disk about the axis of rotation of the first disk.

\* \* \* \* \*